United States Patent
Shinoda et al.

(10) Patent No.: US 10,342,885 B2
(45) Date of Patent: *Jul. 9, 2019

(54) VEHICULAR AIR CLEANER

(75) Inventors: Yoshihisa Shinoda, Susono (JP); Kazuhiro Sugimoto, Susono (JP); Hiroaki Katsumata, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 951 days.

This patent is subject to a terminal disclaimer.

(21) Appl. No.: 14/003,300

(22) PCT Filed: Mar. 31, 2011

(86) PCT No.: PCT/JP2011/058190
§ 371 (c)(1),
(2), (4) Date: Sep. 5, 2013

(87) PCT Pub. No.: WO2012/131967
PCT Pub. Date: Oct. 4, 2012

(65) Prior Publication Data
US 2014/0037508 A1    Feb. 6, 2014

(51) Int. Cl.
*A61L 9/00* (2006.01)
*B01D 53/66* (2006.01)

(52) U.S. Cl.
CPC .............. *A61L 9/00* (2013.01); *B01D 53/66* (2013.01); *B01D 2253/102* (2013.01);
(Continued)

(58) Field of Classification Search
CPC ...... B01D 46/52; B01D 53/74; B01D 53/454; B01D 53/885; B01D 53/8675; A61L 9/00
See application file for complete search history.

(56) References Cited

U.S. PATENT DOCUMENTS

| 6,199,397 B1 | 3/2001 | Khelifa et al. |
| 6,200,542 B1 | 3/2001 | Poles et al. |

(Continued)

FOREIGN PATENT DOCUMENTS

| CN | 1213984 A | 4/1999 |
| DE | 36 17 481 A1 | 11/1988 |

(Continued)

OTHER PUBLICATIONS

Office Action issued in U.S. Appl. No. 14/130,408 dated Oct. 17, 2014.

(Continued)

*Primary Examiner* — Jason M Greene
(74) *Attorney, Agent, or Firm* — Finnegan, Henderson, Farabow, Garrett & Dunner, LLP

(57) ABSTRACT

The present invention relates to a vehicular air cleaner. It is an object to provide a DOR system which can utilize a purifying function of an ozone purifying element containing an activated carbon for a long period of time. As shown in A1 and A2 of FIG. 5, in the activated carbon at an initial state, an ozone purification rate is almost the same as the same wind velocity even when a temperature condition is different, even though the ozone purification rate is changed when the wind velocity is changed. After the endurance test, the ozone purification rate is increased even at the same wind velocity when the temperature becomes high as shown in B1 and B2 of FIG. 5. Thus, the temperature condition difference affects the ozone purification rate more as the deterioration o the activated carbon continues.

6 Claims, 9 Drawing Sheets

(52) U.S. Cl.
CPC .... *B01D 2257/106* (2013.01); *B01D 2258/06* (2013.01); *B01D 2259/4566* (2013.01); *Y02A 50/2347* (2018.01)

(56) References Cited

U.S. PATENT DOCUMENTS

| | | | |
|---|---|---|---|
| 6,280,691 B1 | 8/2001 | Homeyer et al. | |
| 6,616,903 B2* | 9/2003 | Poles | B01D 46/0052 422/108 |
| 9,034,274 B2 | 5/2015 | Shinoda et al. | |
| 2001/0019707 A1 | 9/2001 | Okayama et al. | |
| 2001/0025484 A1 | 10/2001 | Ueno et al. | |
| 2002/0172633 A1* | 11/2002 | Koermer | B01D 53/06 423/219 |
| 2003/0056496 A1 | 3/2003 | Ueno et al. | |
| 2004/0145853 A1* | 7/2004 | Sekoguchi | A61L 9/22 361/225 |
| 2004/0159335 A1* | 8/2004 | Montierth | B08B 3/08 134/10 |
| 2005/0100492 A1* | 5/2005 | Hoke | B01D 53/02 423/219 |
| 2005/0123455 A1* | 6/2005 | Inaba | A61L 9/015 422/120 |
| 2009/0013686 A1 | 1/2009 | Yaguchi et al. | |
| 2010/0067560 A1 | 3/2010 | Kouda et al. | |
| 2010/0254868 A1 | 10/2010 | Obee et al. | |
| 2011/0100331 A1* | 5/2011 | Asada | F02D 11/105 123/478 |
| 2014/0134056 A1 | 5/2014 | Shinoda et al. | |
| 2015/0007731 A1 | 1/2015 | Shinoda | |

FOREIGN PATENT DOCUMENTS

| | | |
|---|---|---|
| DE | 4007965 A1 | 9/1991 |
| DE | 196 24 216 A1 | 1/1998 |
| DE | 198 06 880 A1 | 8/1999 |
| DE | 199 55 253 A1 | 6/2001 |
| FR | 2 848 500 A1 | 6/2004 |
| JP | 59-80739 | 5/1984 |
| JP | 11-507289 | 6/1999 |
| JP | 2000-107545 A | 4/2000 |
| JP | 2001-323811 | 11/2001 |
| JP | 2001-347829 | 12/2001 |
| JP | 2002-514966 | 5/2002 |
| JP | 2003-155924 | 5/2003 |
| JP | 2004-321920 | 11/2004 |
| JP | 2010-848 A | 1/2010 |
| JP | 2010-029816 | 2/2010 |
| JP | 2010-071080 | 4/2010 |
| WO | WO 96/22146 | 7/1996 |
| WO | WO 96/22150 | 7/1996 |
| WO | WO 97/11769 A1 | 4/1997 |
| WO | WO 00/69555 | 11/2000 |
| WO | 2012/127645 A1 | 9/2012 |
| WO | WO 2012/127643 A1 | 9/2012 |

OTHER PUBLICATIONS

Final Office Action issued in U.S. Appl. No. 14/130,408 dated Apr. 20, 2015.

Notice of Allowance issued in U.S. Appl. No. 14/130,408 dated Jul. 14, 2015.

* cited by examiner

VEHICULAR AIR CLEANER

CROSS-REFERENCE TO RELATED APPLICATIONS

This application is a national phase application of International Application No. PCT/JP2011/058190, filed Mar. 31, 2011, the content of which is incorporated herein by reference.

TECHNICAL FIELD

The present invention relates to a vehicular air cleaner, more particularly, to a vehicular air cleaner capable of purifying ozone in air.

BACKGROUND ART

Ozone, which causes photochemical smog, is produced by a photochemical reaction of HC and NOx contained in exhaust gas from automobiles and factories. Therefore, reducing the amount of HC and NOx emissions from automobiles is an efficient way to suppress the production of ozone and prevent the occurrence of photochemical smog. Also, purifying ozone in air directly can be one of the ways to prevent the occurrence of photochemical smog. The occurrence of photochemical smog can be prevented more effectively not only by reducing the amount of emissions of reactants such as HC and NOx, but also by purifying a product such as ozone. Thus, an automobile provided with a vehicular air cleaner capable of directly purifying ozone in air has been put into practical use in some places including California in the United States of America. Such a vehicular air cleaner is particularly called as a DOR (Direct Ozone Reduction) system.

For example, Patent Literature 1 discloses a DOR system in which a vehicle component part such as a condenser of an air conditioner carries a metal oxide such as manganese dioxide. The condenser of the air conditioner is disposed at such a position as to be exposed to air during travel of a vehicle, and the manganese dioxide has a function of converting ozone contained in the air into other elements such as oxygen to purify the ozone. Thus, according to the DOR system disclosed in Patent Literature 1, ozone in air can be directly purified while the vehicle is moving.

CITATION LIST

Patent Literature

Patent Literature 1: National Publication of International Patent Application No. 2002-514966

SUMMARY OF INVENTION

It has been known that not only metal oxide such as manganese dioxide but also activated carbon has a function of purifying ozone. Since the activated carbon has the function of purifying ozone as well as the metal oxide and is available at moderate price, it has been expected to be used as an alternative to the metal oxide. The activated carbon can purify ozone at ambient temperature (25° C.) and thus has an advantage over the metal oxide which purifies ozone at a higher temperature than the ambient temperature. However, there is a problem that the activated carbon is used as an ozone purifying element, its purifying function is easily deteriorated.

Replacing the vehicle component part is one of the countermeasures that combat the deterioration in the ozone purifying function of the activated carbon. However, for example, the condenser of the air conditioner constitutes part of a refrigerant circulation circuit, and thus troublesome work is needed to replace the condenser itself independently. Accordingly, when the ozone purifying element containing the activated carbon is carried on the vehicle component part, it is necessary to countermeasure in utilizing its purifying function as much as possible.

The present invention has been made in view of the above-described circumstances. It is an object to provide a DOR system which can utilize the purifying function of the ozone purifying element containing the activated carbon for a long period of time.

Means for Solving the Problem

To achieve the above mentioned purpose, a first aspect of the present invention is a vehicular air cleaner, comprising:
a vehicle component part arranged on a portion where an air flow passage is formed during travel of a vehicle;
an ozone purifying element provided in the vehicle component part and containing an activated carbon; and
purifying function recovery control means that executes a purifying function recovery control for increasing a temperature of the ozone purifying element in accordance with a degree of deterioration of the ozone purifying element.

A second aspect of the present invention is the vehicular air cleaner according to the first aspect, wherein the purifying function recovery control means inhibits the execution of the purifying function recovery control until the degree of the deterioration of the ozone purifying element exceeds a reference value.

A third aspect of the present invention is the vehicular air cleaner according to the first or the second aspect, further comprising:
ozone concentration acquiring means that acquires an ozone concentration in air; and
ozone concentration comparing means that compares the ozone concentration with a set concentration,
wherein the purifying function recovery control means inhibits the execution of the purifying function recovery control when the ozone concentration is lower than the set concentration.

A forth aspect of the present invention is the vehicular air cleaner according to any one of the first to the third aspect, wherein the vehicle component part is a condenser of the air conditioner, and further comprising temperature difference determining means that determines whether a temperature difference between a required temperature for the air conditioner and an in-vehicle temperature is within a set temperature range, and wherein the purifying function recovery control means stops the purifying function recovery control when the temperature difference after elapse of a set time from start of the execution of the purifying function recovery control gets out of the set temperature range.

Advantageous Effects of Invention

According to the first aspect of the present invention, the purifying function recovery control for increasing the temperature of the ozone purifying element in accordance with the degree of deterioration of the ozone purifying element can be executed. When the temperature of the ozone purifying element is increased, the temperature of air passing through the ozone purifying element becomes high. Accordingly, a probability that the air contacts with the ozone purifying element is increased, and therefore an ozone purification rate of the ozone purifying element is increased. Also, the ozone purification rate of the ozone purifying element is increased as the deterioration of the ozone purifying element continues. Thus, a purifying function of the ozone purifying element can be utilized as much as possible in accordance with the degree of the deterioration of the ozone purifying element according to the present invention.

As described above, the ozone purification rate of the ozone purifying element is increased as the temperature of the ozone purifying element is increased. However, the life of the ozone purifying element may be shortened by executing the purifying function recovery control because the increased temperature of the ozone purifying element may accelerate the progression of its deterioration. In this regard, the second aspect of the present invention inhibits the execution of the purifying function recovery control until the degree of the deterioration of the ozone purifying element exceeds the reference value. Thus, a needless acceleration of the progression of the deterioration of the ozone purifying element can be inhibited. Thus, the life of the ozone purifying element can be extended according to the present invention.

According to the third aspect of the present invention, the execution of the purifying function recovery control can be inhibited when the ozone concentration is lower than the set concentration. Under the environmental condition that the ozone concentration in air is low, ozone purifying efficiency by execution of the purifying function recovery control is relatively low. Thus, the life of the ozone purifying element can be extended by effectively executing the control according to the present invention.

When the vehicle component part is the condenser of the air conditioner, the temperature of the condenser becomes high when the temperature of the ozone purifying element is increased by execution of the purifying function recovery control. Accordingly, the in-vehicle temperature may not reach the required temperature. According to the fourth aspect of the present invention, the execution of the purifying function recovery control can be stopped when the temperature difference between the required temperature for the air conditioner and the in-vehicle temperature after elapse of the set time from start of the purifying function recovery control gets out of the set temperature range. Thus, when the temperature difference is not within the set temperature range, a request for cooling the vehicle can be prioritized and the in-vehicle temperature can quickly reach the required temperature.

DESCRIPTION OF EMBODIMENTS

First Embodiment

[Structure of Vehicular Air Cleaner]

Figure 1:
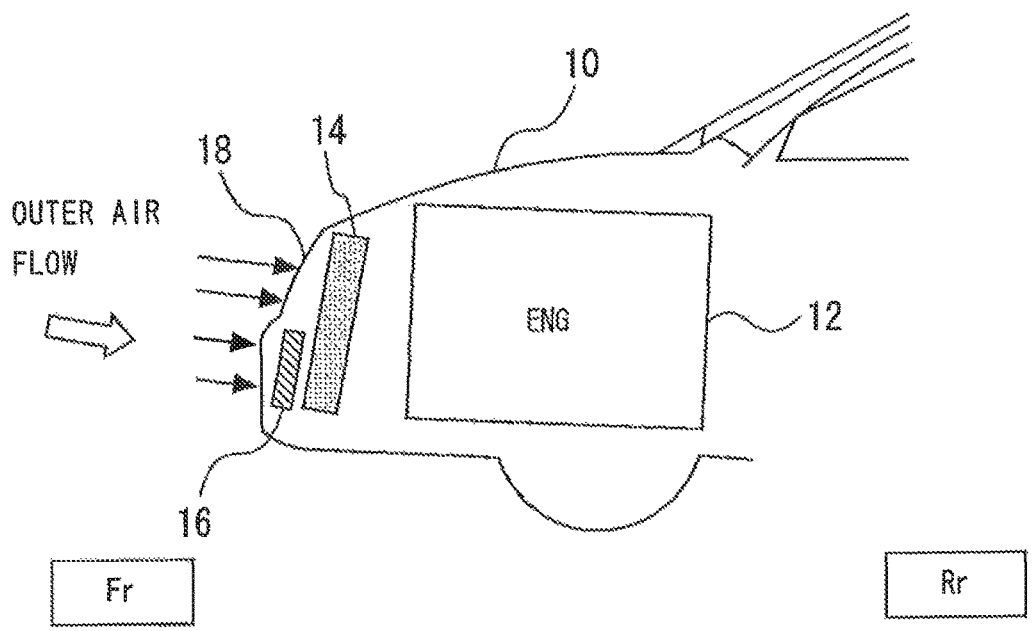
FIG. 1 is a schematic view showing a structure of a vehicle 10 on which an air cleaner according to each embodiment of the present invention is applied.

A first embodiment of the present invention will be explained below with reference to FIGS. 1 to 7. FIG. 1 is a schematic view showing a structure of a vehicle on which an air cleaner is mounted according to the first embodiment. The vehicle 10 includes an internal combustion 12 serving as a power unit. The exhaust gas discharged from the internal combustion 12 contains HC and NOx. Ozone is produced by a photochemical reaction between HC and NOx as reactants. Therefore, when the air cleaner is mounted on the vehicle 10 including the internal combustion 12, the ozone is purified while the vehicle 10 is moving. And thus, the damage to the environment caused due to the vehicle 10 can be reduced.

In the vehicle 10, a radiator 14 for cooling coolant water circulating through the internal combustion 12 is arranged on the front side of the internal combustion 12. A condenser 16 of an air conditioner is arranged on the front side of the radiator 14. An activated carbon serving as an ozone purifying element is provided at a core part of the condenser 16. As shown by arrows in FIG. 1, outer air is taken in through a bumper grill 18 arranged on a front surface of the vehicle 10 during travel of the vehicle 10 and the taken air is delivered through the condenser 16 and the radiator 14 in this order to be discharged to the rear side.

Figure 2:
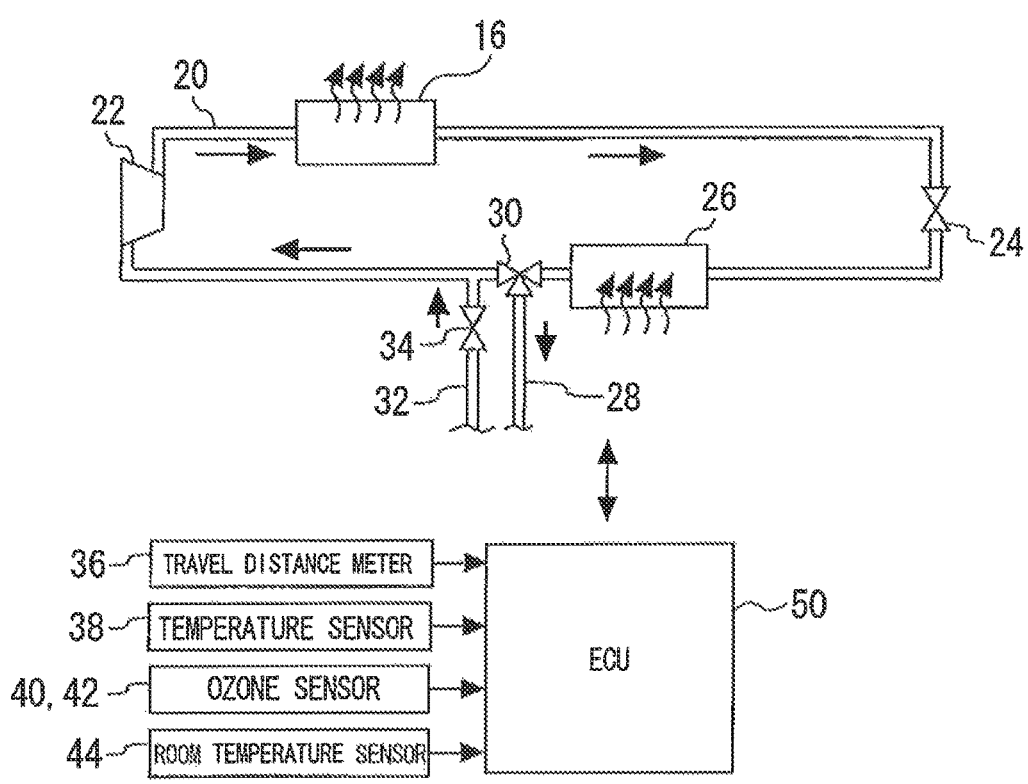
FIG. 2 is a schematic view showing an air conditioning system.

The vehicle 10 includes an air conditioning system constituting part of the air cleaner according to the first embodiment. FIG. 2 is a schematic view showing the air conditioning system. The air conditioning system is a system for conditioning air in the vehicle 10. The air conditioning system includes a refrigerant circulation circuit 20 for circulating a refrigerant such as carbon dioxide. The condenser 16, a compressor 22, an expansion valve 24, and an evaporator 26 are provided in the refrigerant circulation circuit 20. The compressor 22 is used for compressing the refrigerant. The condenser 16 has a function of condensing the refrigerant compressed by the compressor 22. The expansion valve 24 is used for depressurizing the refrigerant condensed by the condenser 16 by throttle expansion. The evaporator 26 is used for evaporating the refrigerant depressurized by the expansion valve 24.

As shown by arrows in FIG. 2, the refrigerant circulates through the compressor 22, the condenser 16, the expansion valve 24, and the evaporator 26 in this order. The refrigerant is compressed when passing through the compressor 22 to be in a high-temperature and high-pressure state, and is condensed when passing through the condenser 16 to be in a low-temperature and high-pressure state. Also, the refrigerant is depressurized by the expansion valve 24 to be in a low-temperature and low-pressure state, and is evaporated by the evaporator 26 to be in a high-temperature and low-pressure state. The refrigerant, which is in the high-temperature and low-pressure state by the evaporator 26, is delivered through the refrigerant circulation circuit 20 to be introduced into the compressor 22 and is compressed by the compressor 22.

The air conditioning system shown in FIG. 2 further includes a refrigerant introduction path 28, a three-way valve 30, a refrigerant return path 32, and a refrigerant opening and closing valve 34. The refrigerant introduction path 28 is connected to the refrigerant circulation circuit 20 between the compressor 22 and the evaporator 26 via the three-way valve 30. The three-way valve 30 is adapted to connect or interrupt the refrigerant circulation circuit 20 and the refrigerant introduction path 28. The refrigerant return path 32 is connected to the refrigerant circulation circuit 20 on the upstream side of the three-way valve 30. The refrigerant opening and closing valve 34 is provided in the refrigerant return path 32, and is adapted to and able to open and close the refrigerant return path 32 by the opening and closing operation.

When the three-way valve 30 is operated to connect the refrigerant circulation circuit 20 and the refrigerant introduction path 28, the refrigerant flowing through the refrigerant circulation circuit 20 is introduced into the refrigerant introduction path 28 as shown by an arrow in FIG. 2. Also, when the refrigerant opening and closing valve 34 is opened, the refrigerant flowing through the refrigerant return path 32 is introduced into the refrigerant circulation circuit 20.

Further, as shown in FIG. 2, the air cleaner according to the first embodiment includes an ECU (Electronic Control Unit) 50 as a control unit. The compressor 22, the expansion 24, the three-way valve 30, the refrigerant opening and closing valve 34 and the like are connected to an output side of the ECU 50. A travel distance meter 36 for measuring a vehicle travel distance at a present moment, a temperature sensor 38 for detecting the temperature of the condenser 16, ozone sensors 40 and 42 for detecting the ozone concentration at the front and rear sides of the condenser 16, and a room temperature sensor 44 for detecting the in-vehicle temperature are connected to an input side of the ECU 50. The ECU 50 is configured to control various actuators such as the compressor 22 based on a signal from the travel distance meter 36 or the like.

[Characteristics of First Embodiment]

Figure 3:
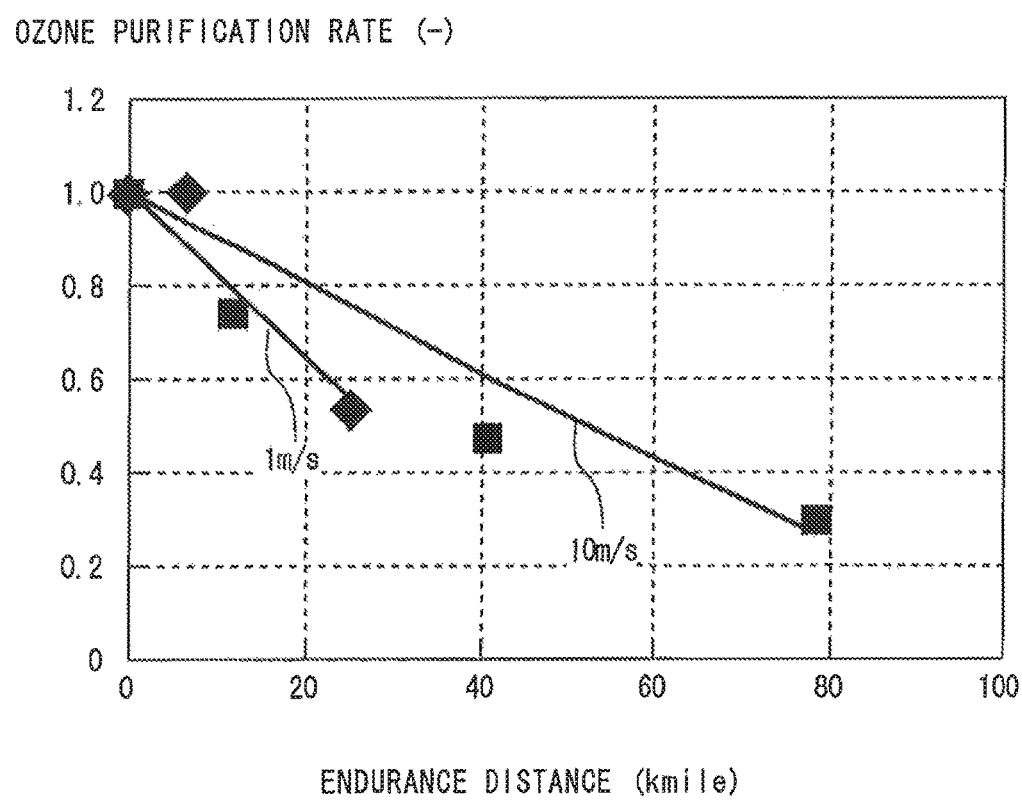
FIG. 3 shows data of results of an ozone purification endurance test of activated carbon.

FIG. 3 shows data of results of an ozone purification endurance test of activated carbon. In FIG. 3, the horizontal axis represents an endurance distance (kilomile) and the vertical axis represents a relative value based on an ozone purification rate at an initial state (when the endurance distance is 0 kilomile). The data shown in FIG. 3 is obtained by preparing two activated carbons of equivalent sizes and specific surface areas, and then measuring the rear side ozone concentration of these activated carbons when a gas containing ozone having a predetermined concentration passes through these activated carbons from the front side toward the rear side at different velocities (wind velocities of 1 m/s and 10 m/s).

As shown in FIG. 3, the ozone purification rate of the activated carbon is reduced as the endurance distance becomes longer. Also, as shown in FIG. 3, the degree of reduction of the ozone purification rate of the activated carbon is changed depending on the wind velocity of the passing gas containing ozone. More specifically, in the case where the gas containing ozone passes at the wind velocity of 1 m/s, the ozone purification rate goes down by half from the ozone purification rate at the initial state when the endurance distance is approximately 30 kilomiles. In the case where the gas containing ozone passes at the wind velocity of 10 m/s, the ozone purification rate remains at about 70% or more of the ozone purification rate at the initial state when the endurance distance is approximately 30 kilomiles, and then goes down by half from the purification rate at the initial state when the endurance distance is approximately 60 kilomiles. In other words, the degree of reduction of the ozone purification rate is smaller when the gas passes at high speed (wind velocity of 10 m/s) as compared to when the gas passes at low speed (wind velocity of 1 m/s).

Figure 4:
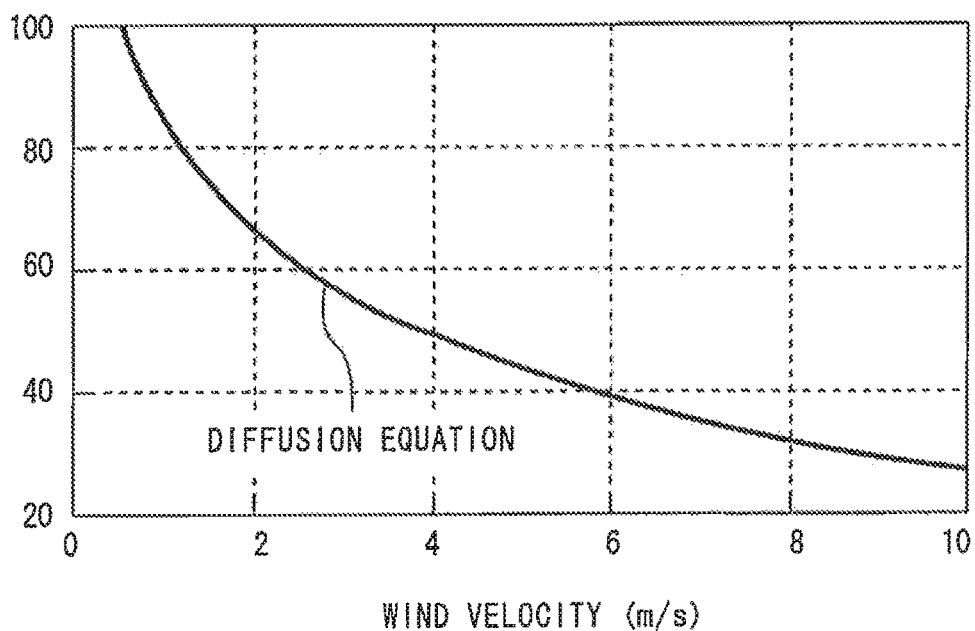
FIG. 4 shows a relationship between the wind velocity of gas passing through the condenser and a probability that the gas is contacted with the condenser.

FIG. 4 is a graph showing a relationship between the wind velocity of gas passing through a condenser and the probability that the gas is contacted with the condenser. This graph is provided by applying the Gormley-Kennedy diffusion equation to a model of an aluminum honeycomb radiator. As shown in FIG. 4, the probability that the gas is contacted with the radiator is approximately 100% when the wind velocity is approximately 1 m/s. Also, the probability that the gas is contacted with the radiator is decreased to approximately 10% when the wind velocity is approximately 10 m/s. In other words, the probability that the gas is contacted with the radiator is high when the wind velocity is slow, and is gradually lowered as the wind velocity is faster. The relationship shown in FIG. 4 can be applied to the condenser because the condenser 16 is positioned on the front side of the radiator 14 in the vehicle 10. Thus, it can be found that the probability that the gas is contacted with the condenser (hereinafter referred to as "gas contact probability") is high when the wind velocity of the gas passing through the condenser is slow, and is gradually lowered as the wind velocity is faster.

From the graphs shown in FIGS. 3 and 4, it is found that the ozone purification rate of the activated carbon and the gas contact probability correlate with each other. It is found from the graph shown in FIG. 4 that the gas contact probability is higher as the wind velocity is slower and the gas contact probability is lower as the wind velocity is faster. Also, it is found from the graph shown in FIG. 3 that the degree of reduction of the ozone purification rate is larger as the wind velocity is slower and the degree of reduction of the ozone purification rate is smaller as the wind velocity is faster. Thus, from the graphs shown in FIGS. 3 and 4, it is obvious that the degree of reduction of the ozone purification rate of the activated carbon is greater as the gas contact probability is higher and the degree of reduction of the ozone purification rate of the activated carbon is lesser as the gas contact probability is lower.

Figure 5:
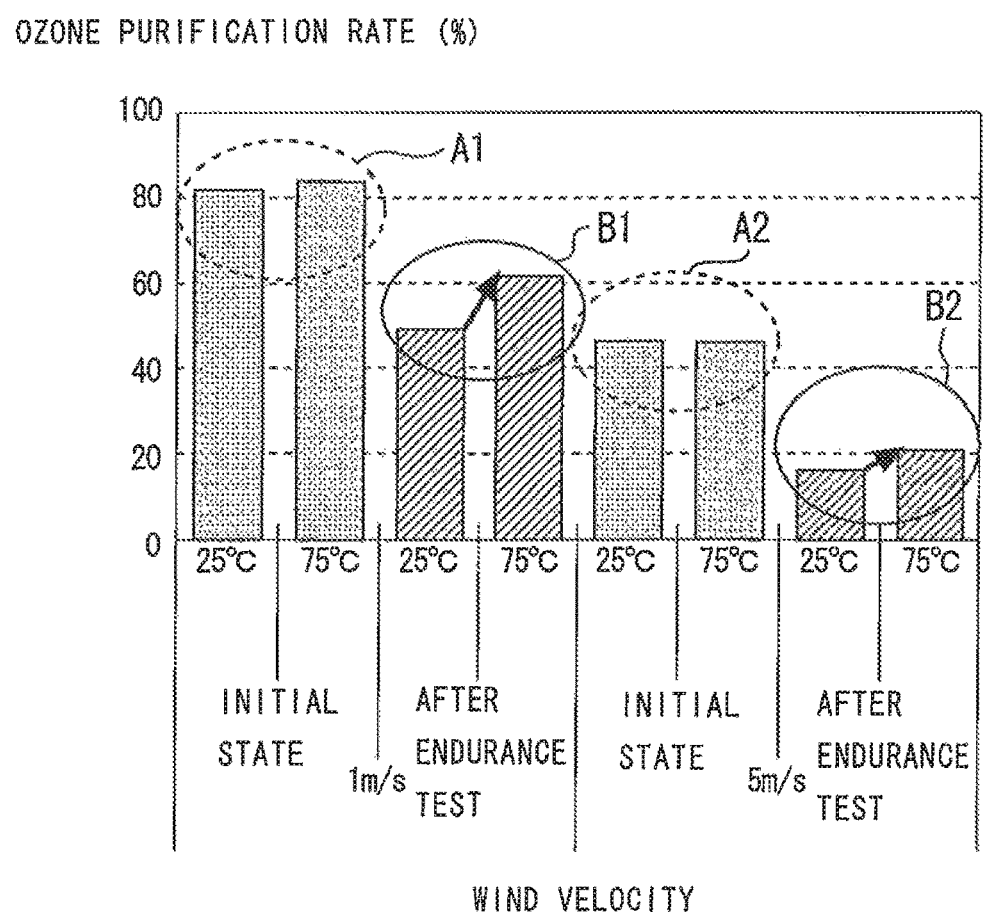
FIG. 5 is a graph showing changes of temperature characteristics before and after the endurance test of the ozone purification rate of the activated carbon.

Incidentally, FIG. 5 is a graph showing changes of temperature characteristics before and after the endurance test of the ozone purification rate of the activated carbon. The graph shown in FIG. 5 is made by preparing activated carbons (of equivalent sizes and specific surface areas) at the initial state (when the endurance distance is 0 kilomile) and after the endurance test (when the endurance distance is 50 kilomile), and then measuring the rear side ozone concentration of these activated carbons when a gas containing ozone having a predetermined concentration passes through the activated carbons from the front side toward the rear side at different velocities (wind velocities of 1 m/s and 5 m/s) under different temperature conditions (25° C. and 75° C.).

In general, as a temperature of gas becomes higher, its mobility becomes more active. Therefore, when the temperature of the activated carbon is increased, the gas passing through the activated carbon becomes high and thus the gas contact probability is increased. However, at the initial state, the ozone purification rate is almost the same at the same wind velocity even when the temperature condition is different as shown in A1 and A2 of FIG. 5, even though the ozone purification rate is changed when the wind velocity is changed. Consequently, it is found that, at the initial state, the temperature difference hardly affects the ozone purification rate. On the other hand, after the endurance test, the ozone purification rate is increased even at the same wind velocity when the temperature becomes high as shown in B1 and B2 of FIG. 5. Thus, it can be found from FIG. 5 that the temperature difference affects the ozone purification rate more as the deterioration of the activated carbon continues.

Figure 6:
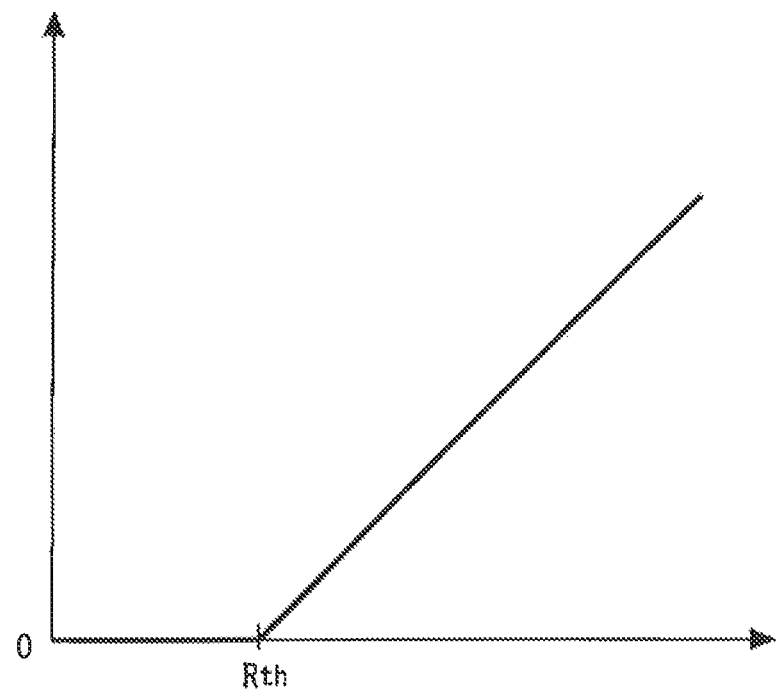
FIG. 6 is an illustration for explaining an outline of the purifying function recovery control according to a first embodiment.

Based on foregoing knowledge, in the first embodiment, a control for increasing the pressure of the compressor 22 is executed and the temperature of the condenser 16 is increased in accordance with the deterioration rate when a deterioration rate of the activated carbon is higher than a predetermined value (purifying function recovery control). FIG. 6 is an illustration for explaining an outline of the purifying function recovery control according to the first embodiment. In FIG. 6, the horizontal axis represents a deterioration rate R of the activated carbon and the vertical axis represents an increased pressure of the compressor 22 (referred to as "ozone purifying function demand pressure $P_{O3}$").

As shown in FIG. 6, the purifying function recovery control is executed such that the ozone purifying function demand pressure $P_{O3}$ is increased as the deterioration rate R of the activated carbon is increased. In other words, the compressor 22 is controlled such that the temperature of the condenser 16 is increased as the deterioration rate R of the activated carbon is increased. This will make it possible to raise the pressure of the compressor 22 and thus, the ozone purification rate of the activated carbon can be increased.

The purifying function recovery control is executed only when the deterioration rate R of the activated carbon is higher than a predetermined value $R_{th}$. In other words, the purifying function recovery control is not executed when the deterioration rate R of the activated carbon is lower than the predetermined value $R_{th}$. As described above with reference to FIG. 5, when the temperature of the activated carbon is high, the temperature of the gas passing through the activated carbon becomes high, and accordingly, the gas contact probability is increased. Thus, when the purifying function recovery control is executed, the ozone purification rate of the activated carbon can be increased while the deterioration of the activated carbon easily continues. In this regard, the purifying function recovery control is not executed when the deterioration rate R of the activated carbon is lower than the predetermined value $R_{th}$ and therefore the progression of the deterioration of the activated carbon can be suppressed. In addition, the fuel consumption may be deteriorated since the fuel in consumed in accordance with the increased pressure of the compressor 22 for executing the purifying function recovery control. Therefore, when the purifying function recovery control is not executed in the case where the deterioration rate R of the activated carbon is lower than the predetermined value $R_{th}$, the deterioration of the fuel consumption can be suppressed. Thus, the life of the activated carbon can be extended and its purifying function can be utilized as much as possible.

The deterioration rate R of the activated carbon is calculated by adding a correction value calculated based on an ozone concentration ratio on upstream and downstream of the condenser 16 (referred to as "concentration correction value") and a correction value based on an average value of a temperature history of the 16 condenser (referred to as "temperature history correction value") to a reference value calculated in accordance with the travel distance of the vehicle 10. The ECU 50 stores map data into which a relationship between the reference value and the vehicle travel distance is converted in advance. The ECU 50 also stores map data into which a relationship between the concentration correction value and the ozone concentration ratio and a relationship between the temperature history correction value and the average value of the temperature history are converted in advance.

[Specific Processing of First Embodiment]

Figure 7:
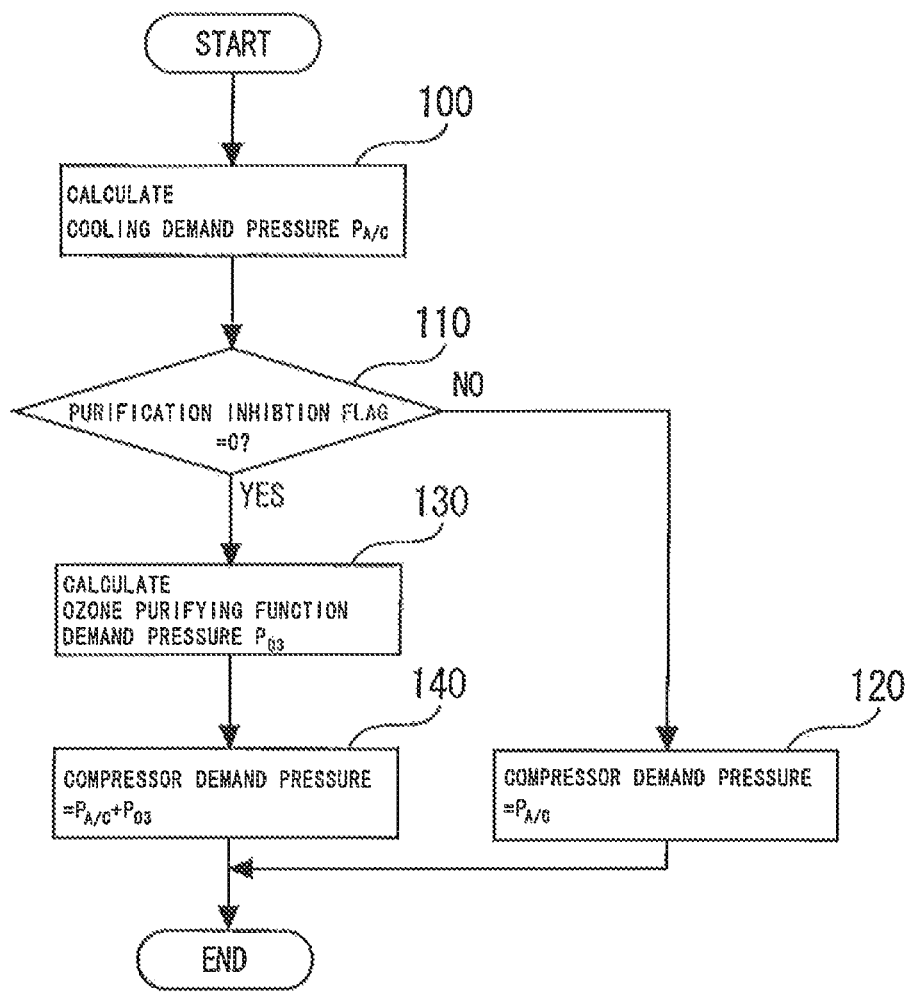
FIG. 7 is a flow chart showing the purifying function recovery control executed by the ECU 50 according to the first embodiment.

Next, a specific processing for executing the purifying function recovery control described above will be explained with reference to FIG. 7. FIG. 7 is a flow chart showing the purifying function recovery control executed by the ECU 50 according to the first embodiment. Incidentally, the routine shown in FIG. 7 is repeatedly executed at regular intervals.

In the routine shown in FIG. 7, the ECU 50 firstly calculates cooling demand pressure $P_{A/C}$ for the air conditioning system (step 100). The cooling demand pressure $P_{A/C}$ is pressure of the compressor 22 corresponding to an in-vehicle temperature set by a driver of the vehicle 10 (hereinafter referred to as "required temperature $T_{rq}$") and is converted into map data in advance to be stored in the ECU 50. In this step, the ECU 50 reads the cooling demand pressure $P_{A/C}$ corresponding to the required temperature $T_{rq}$ with reference to the map data. Incidentally, when the air conditioner is turned off, i.e., when the in-vehicle temperature is not set, the cooling demand pressure $P_{A/C}$ is zero.

Next, the ECU 50 determines whether a purification inhibiting flag is 0 or not (step 110). The purification inhibiting flag is set to be 1 under the condition that the execution of the purifying function recovery control is inhibited, and is set to be 0 under the condition that the execution of the purifying function recovery control is permitted in later-described second and third embodiments. This purification inhibiting flag is reset to be 0 when the internal combustion 12 is stopped.

When it is determined that the purification inhibiting flag is 1 in the step 110, the ECU 50 sets a compressor demand pressure $P_{COM}$ to the cooling demand pressure $P_{A/C}$ calculated in the step 100 (step 120). When it is determined that the purification inhibiting flag is 0 in the step 110, the ECU 50 calculates an ozone purifying function demand pressure $P_{O3}$ (step 130). More specifically, the ECU 50 reads the reference value with reference to the map data defining the relationship between the detected value of the travel distance meter 36 and the reference value. At the same time, the ECU 50 reads the concentration correction value and the temperature history correction value with reference to each map data. Then, the ECU 50 calculates the ozone purifying function demand pressure $P_{O3}$ based on these values.

Subsequently to the step 130, the ECU 50 calculates the compressor demand pressure $P_{COM}$ (step 140). More specifically, the ECU 50 adds the cooling demand pressure $P_{A/C}$ calculated in the step 100 and the ozone purifying function demand pressure $P_{O3}$ calculated in the step 120. Then, the compressor 22 is operated by the compressor demand pressure $P_{COM}$ calculated in the step 140 or the step 120.

According to the routine shown in FIG. 7 as described above, when it is determined that the purification inhibiting flag is 0, the operation pressure of the compressor 22 can be controlled to be the compressor demand pressure $P_{COM}$ obtained by adding the ozone purifying function demand pressure $P_{O3}$ to the cooling demand pressure $P_{A/C}$. Therefore, the ozone purification rate of the activated carbon can be increased in accordance with the deterioration rate R of the activated carbon under the condition that the execution of the purifying function recovery control is permitted. Thus, the life of the activated carbon can be extended and its purifying function can be utilized as much as possible.

In the first embodiment, incidentally, the activated carbon is used as the ozone purifying element. However, an elemental metal such as manganese, iron, cobalt, nickel, copper, ruthenium, rhodium, palladium, silver, platinum, and gold, a metal complex or organometallic complex including one of these elemental metals as a center metal, or zeolite may be used with the activated carbon as the ozon purifying element. These elemental metals, the metal complex, organometallic complex, or zeolite have an ozone purifying function just like the activated carbon. Thus, by using them with the activated carbon, the deterioration of the ozone purifying function of the activated carbon can be suppressed. Also, a metal oxide such as manganese dioxide may be used with the activated carbon. Two types or more of these alternative elements may be used in combination. This modification is similarly applicable to the later-described second and third embodiments.

Although the activated carbon is provided at the core part of the condenser 16 in the first embodiment, the activated carbon may be provided at the core part of the radiator 14 instead of the core part of the condenser 16. Also, the activated carbon may be provided at the core parts of both radiator 14 and condenser 16. Since an average value of the operating temperature of the radiator is higher than that of the condenser (radiator: 75° C. to 95° C., condenser: 60° C. to 80° C.), the temperature of air passing through the radiator is higher than the temperature of air passing through the condenser. Accordingly, the probability that the air is contacted with the radiator 14 is higher than the probability that the air is contacted with the condenser 16. Thus, the degree of reduction of the ozone purification rate of the activated carbon provided at the core part of the radiator 14 will be larger than that of the activated carbon provided at the core part of the condenser 16 (see FIGS. 3 and 4).

It is preferable that the activated carbon is provided at the core part of the condenser 16 to extend the life of the activated carbon. However, even when the activated carbon is provided at the core part of the radiator 14, the advantageous effects obtained when the activated carbon is provided at the core part of the condenser 16 can be obtained by executing the above-described purifying function recovery control. Thus, the activated carbon may be provided at the core part of the radiator 14 instead of the core part of the condenser 16, or at the core parts of both radiator 14 and condenser 16. Incidentally, this modification is similarly applicable to the later-described second and third embodiments.

In the first embodiment, the ECU 50 increases the pressure of the compressor 22 to increase the temperature of the condenser 16 during the purifying function recovery control. However, means for heating the condenser 16 is not limited thereto. For example, the condenser 16 may be heated by utilizing the exhaust heat of the internal combustion 12. Alternatively, the condenser 16 may be heated by a heating apparatus such as a heater provided separately.

In the first embodiment, the deterioration rate R of the activated carbon is calculated by adding the concentration correction value and the temperature history correction value to the reference value calculated in accordance with the travel distance of the vehicle 10. However, the deterioration rate R of the activated carbon may be calculated only based on the reference value, or may be calculated by adding only the concentration correction value to the reference value. Further, the deterioration rate R of the activated carbon may be calculated only based on the concentration correction value. This means that the deterioration rate R of the activated carbon may be calculated by using at least one parameter of the reference value, the concentration correction value, and the temperature history correction value. Alternatively, the deterioration rate R of the activated carbon may be calculated by using other parameter in addition to these parameters. This modification is similarly applicable to the later-described second and third embodiments.

In the first embodiment, the condenser 16 corresponds to "the vehicle component part" according to the first aspect of the present invention. Also, in the first embodiment, "the purifying function recovery control means" according to the first aspect of the present invention is implemented when the ECU 50 executes a series of processing shown in FIG. 7.

Second Embodiment

Figure 8:
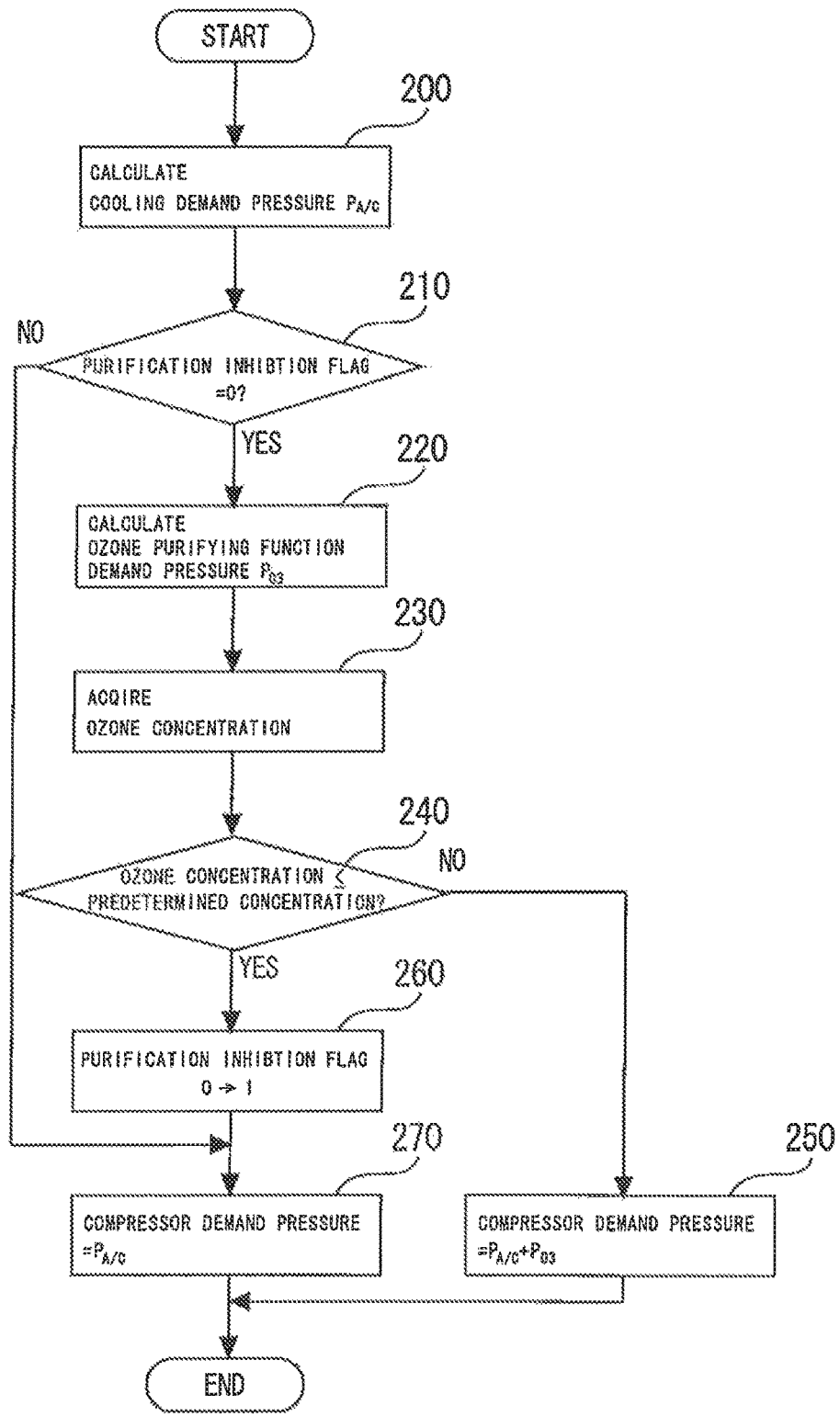
FIG. 8 is a flow chart showing the purifying function recovery control executed by the ECU 50 according to a second embodiment.

Next, the second embodiment of the present invention will be explained below with reference to FIG. 8. In the second embodiment, the purifying function recovery control shown in FIG. 8 is executed with the structure shown in FIGS. 1 and 2. Thus, differences from the first embodiment will be mainly explained below, and a detailed explanation of similar features will be simplified or omitted.

[Characteristics of Second Embodiment]

In the first embodiment, the ozone purification rate of the activated carbon is increased by increasing the pressure of the compressor 22, which has been described as the purifying function recovery control, when the deterioration rate R of the activated carbon is higher than the predetermined value $R_{th}$. However, the execution of the fuel consumption may be deteriorated, which is described above, because the fuel is consumed in accordance with the increased pressure of the compressor 22 for executing the purifying function recovery control. Therefore, in the second embodiment, the execution of the purifying function recovery control is inhibited under the environmental condition that the ozone concentration in air is low. Under the environmental condition that the ozone concentration in air is low, ozone purifying efficiency by execution of the purifying function recovery control is relatively low. According to the second embodiment, the fuel deterioration caused by execution of the purifying function recovery control can be suppressed while the life of the activated carbon can be extended by effectively executing the control.

[Specific Processing of Second Embodiment]

Next, a specific processing for executing the purifying function recovery control according to the second embodiment will be explained with reference to FIG. 8. FIG. 8 is a flow chart showing the purifying function recovery control executed by the ECU 50 according to the second embodiment. Incidentally, the routine shown in FIG. 8 is repeatedly executed at regular intervals, instead of the routine shown in FIG. 7.

In the routine shown in FIG. 8, the ECU 50 calculates the cooling demand pressure $P_{A/C}$ for the air conditioning system (step 200), and then determines whether the purification inhibiting flag is 0 or not (step 210). When it is determined that the purification inhibiting flag is 1 in the step 210, the ECU 50 sets the compressor demand pressure $P_{COM}$ to the cooling demand pressure $P_{A/C}$ calculated in the step 200 (step 270). On the other hand, when it is determined that the purification inhibiting flag is 0 in the step 210, the ECU 50 calculates the ozone purifying function demand pressure $P_{O3}$ (step 220). A series of processing in the steps 200 to 220 and 270 is the same as the processing in the steps 100 to 130 shown in FIG. 7, and therefore a detailed explanation thereof is omitted here.

Subsequently to the step 220, the ECU 50 acquires an ozone concentration $C_{O3}$ (step 230), and then determines whether the acquired ozone concentration $C_{O3}$ is a predetermined concentration $C_{th}$ or less (step 240). More specifically, the ECU 50 acquires a detected value of the ozone sensor 40, and compares the detected value with the predetermined concentration $C_{th}$ stored in the ECU 50 in advance.

When it is determined that the acquired ozone concentration $C_{O3}$ is higher than the predetermined concentration $C_{th}$ in the step 240, the ECU 50 adds the cooling demand pressure $P_{A/C}$ calculated in the step 200 and the ozone purifying function demand pressure $P_{O3}$ calculated in the step 220 to calculate the compressor demand pressure $P_{COM}$ (step 250). On the other hand, when it is determined that the acquired ozone concentration $C_{O3}$ is the predetermined concentration $C_{th}$ or lower in the step 240, the ECU 50 sets the purification inhibiting flag to be 1 (step 260) and sets the compressor demand pressure $P_{COM}$ to the cooling demand pressure $P_{A/C}$ calculated in the step 200 (step 270).

According to the routine shown in FIG. 8, when the acquired ozone concentration $C_{O3}$ is the predetermined concentration $C_{th}$ or lower, the pressure increase of the compressor 22 for recovering the ozone purifying function is inhibited. Thus, the fuel deterioration due to the pressure increase of the compressor 22 can be suppressed while the life of the activated carbon can be extended by effectively executing the control.

In the second embodiment, incidentally, the ozone concentration is acquired based on the detected value of the ozone sensor 40. However, instead of the detected value of the ozone sensor 40, the ozone concentration may be indirectly acquired based on travel area information relating to the ozone concentration such as navigation information, outer air temperature, seasons, and time. Alternatively, the ozone concentration may be acquired by combining the detected value of the ozone sensor 40 and the travel area information.

In the second embodiment, the ozone sensor 40 corresponds to "the ozone concentration acquiring means" according to the third aspect of the present invention. Also, in the second embodiment, "the ozone concentration comparing means" according to the third aspect of the present invention is implemented when the ECU 50 executes the processing in the step 240 shown in FIG. 8.

Third Embodiment

Figure 9:
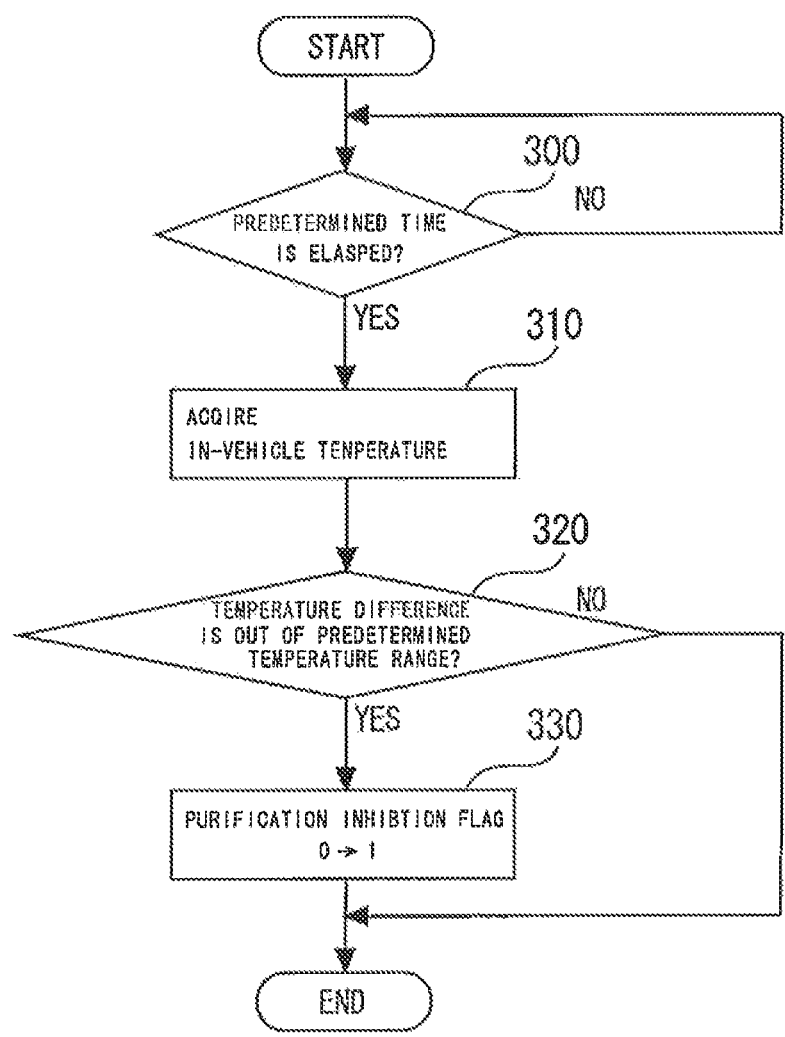
FIG. 9 is a flow chart showing the function recovery stop control executed by the ECU 50 according to a third embodiment.

Next, the third embodiment of the present invention will be explained below with reference to FIG. 9. In the third embodiment, a function recovery stop control shown in FIG. 9 is executed with the structure shown in FIGS. 1 and 2. Thus, differences from the first embodiment will be mainly explained below, and a detailed explanation of similar features will be simplified or omitted.

[Characteristics of Third Embodiment]

The purifying function recovery control adds the ozone purifying function demand pressure $P_{O3}$ to the cooling demand pressure $P_{A/C}$ as described above. Thus, an actual in-vehicle temperature $T_{in}$ may not reach the required temperature $T_{rq}$. Thus, in the third embodiment, when the temperature difference between the in-vehicle temperature $T_{in}$ and the required temperature $T_{rq}$ is still generated after the elapse of a predetermined time from the start of the execution of the purifying function recovery control, the execution of the purifying function recovery control is stopped (function recovery stop control).

[Specific Processing of Third Embodiment]

Next, a specific processing for executing the function recovery stop control will be explained below with reference to FIG. 9. FIG. 9 is a flow chart showing the function recovery stop control executed by the ECU 50 according to the third embodiment. The routine shown in FIG. 9 is executed concurrently every time when the cycling execution of the routine shown in FIG. 7 or 8.

In the routine shown in FIG. 9, the ECU 50 firstly determines whether the predetermined time is elapsed after the purifying function recovery control is started (step 300). More specifically, the ECU 50 counts the elapsed time after the routine shown in FIG. 7 or 8 is started, and then determines whether the elapsed time exceeds the predetermined time. Incidentally, the predetermined time which is applied in this step is set in advance and stored in the ECU 50.

When it is determined that the predetermined time is not elapsed after the purifying function recovery control is started in the step 300, the processing returns to the step 300 to execute the same processing again. On the other hand, when it is determined that the predetermined time is elapsed after the purifying function recovery control is started in the step 300, the ECU 50 acquires the in-vehicle temperature $T_{in}$ (step 310), and then determines whether the temperature difference $T_{in}$-$T_{rq}$ between the in-vehicle temperature $T_{in}$ and the required temperature $T_{rq}$ is within a predetermined temperature range (step 320). More specifically, the ECU 50 acquires a detected value of the room temperature sensor 44, and compares an absolute value of the temperature difference between the detected value and the required temperature $T_{rq}$ with the predetermined temperature $T_{th}$ stored in the ECU 50 in advance.

When it is determined that the temperature difference $T_{in}$-$T_{rq}$ between the in-vehicle temperature $T_{in}$ and the required temperature $T_{rq}$ is not within the predetermined temperature range in the step 320, the ECU 50 sets the purification inhibiting flag to be 1 (step 330). On the other hand, when it is determined that the temperature difference $T_{in}$-$T_{rq}$ between the in-vehicle temperature $T_{in}$ and the required temperature $T_{rq}$ is within the predetermined temperature range, the ECU 50 terminates the routine.

According to the routine shown in FIG. 9, when the temperature difference $T_{in}$ $T_{rq}$ between the in-vehicle temperature $T_{in}$ and the required temperature $T_{rq}$, which is acquired after the elapse of the predetermined time, is not within the predetermined temperature range, the pressure increase of the compressor 22 for recovering the ozone purifying function is inhibited. Thus, a request for cooling the vehicle can be prioritized and the in-vehicle temperature $T_{in}$ can quickly reach the required temperature $T_{rq}$.

In the third embodiment, "the temperature difference determining means" according to the fourth aspect of the present invention is implemented when the processing in the step 320 shown in FIG. 9 is executed.

DESCRIPTION OF REFERENCE NUMERALS 10 vehicle
12 internal combustion
14 radiator
16 condenser
18 bumper grill
20 refrigerant circulation circuit
22 compressor 24 expansion valve
26 evaporator
28 refrigerant introduction path
30 three-way valve
32 refrigerant return path
34 refrigerant opening and closing valve
36 travel distance meter
38 temperature sensor
40, 42 ozone sensor
44 room temperature sensor
50 ECU

The invention claimed is:

1. A vehicular air cleaner, comprising:
a vehicle component part arranged on a portion of a vehicle where an air flow passage is formed during travel of the vehicle;
an ozone purifying element which is provided in the vehicle component part, contains an activated carbon, and has a function of purifying ozone;
an ozone concentration sensor which is configured to detect an ozone concentration in air; and
an electronic control unit which is configured to:
execute a purifying function recovery control of the ozone purifying element, wherein the purifying function recovery control includes increasing a temperature of the ozone purifying element based on a degree of deterioration of the purifying function of the ozone purifying element;
compare the ozone concentration with a set concentration; and
inhibit the execution of the purifying function recovery control when the ozone concentration is lower than the set concentration.

2. The vehicular air cleaner according to claim 1, wherein the electronic control unit is also configured to inhibit the execution of the purifying function recovery control until the degree of deterioration of the purifying function of the ozone purifying element exceeds a reference value.

3. The vehicular air cleaner according to claim 1, wherein:
the vehicle component part is a condenser of an air conditioner, and
the electronic control unit is also configured to:
determine whether a temperature difference between a required temperature for the air conditioner and an in-vehicle temperature is within a set temperature range; and
stop the purifying function recovery control when the temperature difference after elapse of a set time from start of the execution of the purifying function recovery control gets out of the set temperature range.

4. A vehicle, comprising:
a vehicle component part arranged on a portion where an air flow passage is formed during travel of the vehicle;
an ozone purifying element, which is provided in the vehicle component part, contains an activated carbon, and has a function of purifying ozone;
an ozone concentration sensor which is configured to detect an ozone concentration in air; and
an electronic control unit which is configured to:
execute a purifying function recovery control of the ozone purifying element, wherein the purifying function recovery control includes increasing a temperature of the ozone purifying element based on a degree of deterioration of the purifying function of the ozone purifying element;
compare the ozone concentration with a set concentration; and
inhibit the execution of the purifying function recovery control when the ozone concentration is lower than the set concentration.

5. The vehicle according to claim 4, wherein the electronic control unit is also configured to inhibit the execution of the purifying function recovery control until the degree of deterioration of the purifying function of the ozone purifying element exceeds a reference value.

6. The vehicle according to claim 4, wherein:
the vehicle component part is a condenser of an air conditioner, and
the electronic control unit is also configured to:
determine whether a temperature difference between a required temperature for the air conditioner and an in-vehicle temperature is within a set temperature range; and
stop the purifying function recovery control when the temperature difference after elapse of a set time from start of the execution of the purifying function recovery control gets out of the set temperature range.

* * * * *